US008294102B2

(12) United States Patent
Lall

(10) Patent No.: US 8,294,102 B2
(45) Date of Patent: Oct. 23, 2012

(54) TACTICAL CHEMICAL BIOLOGICAL THREAT DETECTION

(76) Inventor: Ravinder P. Lall, Clarksville, MD (US)

( * ) Notice: Subject to any disclaimer, the term of this patent is extended or adjusted under 35 U.S.C. 154(b) by 0 days.

(21) Appl. No.: 13/399,858

(22) Filed: Feb. 17, 2012

(65) Prior Publication Data

US 2012/0217402 A1 Aug. 30, 2012

(51) Int. Cl.
*G01N 21/00* (2006.01)

(52) U.S. Cl. .................................................... 250/338.5

(58) Field of Classification Search .......... 250/330–335, 250/338.1–338.5, 339.01–339.15, 340, 341.1–341.8
See application file for complete search history.

(56) References Cited

U.S. PATENT DOCUMENTS

| | | | | |
|---|---|---|---|---|
| 5,241,179 | A * | 8/1993 | Carrieri | 250/341.6 |
| 5,510,620 | A | 4/1996 | Achter et al. | |
| 5,807,750 | A | 9/1998 | Baum et al. | |
| 6,066,295 | A * | 5/2000 | Bernstein et al. | 422/50 |
| 6,593,582 | B2 * | 7/2003 | Lee et al. | 250/458.1 |
| 6,943,884 | B2 * | 9/2005 | Rice | 356/437 |
| 7,498,574 | B2 * | 3/2009 | Puscasu et al. | 250/336.1 |
| 7,508,520 | B1 * | 3/2009 | Lines et al. | 356/437 |
| 7,616,888 | B2 * | 11/2009 | Mendenhall et al. | 398/25 |
| 7,825,380 | B2 * | 11/2010 | Puscasu et al. | 250/336.1 |
| 7,995,917 | B2 * | 8/2011 | Mendenhall et al. | 398/25 |
| 8,018,647 | B2 * | 9/2011 | Rice et al. | 359/334 |
| 8,101,915 | B2 * | 1/2012 | McGill et al. | 250/338.5 |
| 2008/0185525 | A1 | 8/2008 | Lyubchik et al. | |

OTHER PUBLICATIONS

Thomas et al., “Infrared point sensors for homeland defense applications,” 2004, SPIE Proceedings, V. 5269, p. 150-158.
Bellecci et al., “Database for chemical weapons detection . . . ”, 2008, SPIE Proceedings, V. 7116 p. 71160Q1-10.
D.F. Flanigan, “Hazardous cloud imaging: a new way of using passive IR”, 1997, SPIE Proceedings, V. 3082, pp. 14-21.
J.P. Carrico, “Chemical-biological defense remote sensing: what’s happening,” 1998, SPIE Proceedings, V. 3383, pp. 45-56.

* cited by examiner

*Primary Examiner* — Kiho Kim
(74) *Attorney, Agent, or Firm* — Michael J. Foycik, Jr.

(57) ABSTRACT

This relates to a chemical biological threat detection system for enhancing the, discrimination in chemical biological threat detection in atmospheric air, low level chemical biological threat detection in air, as well as tactical determination of threat chemical biological agents’ concentrations in a specific atmospheric range, at various time intervals. This uses the concept of quantitative monitoring the atmospheric air for chemical biological threats, as well as measuring the quantitative correlations/ratios in differential changes in the air, for the active/passive chemical biological Infrared (IR) EM radiation at an 8-12 μM wavelength, absorption/emission/scattering, using Electro-Optics. This chemical biological solution will use the reference chemical biological IR EM radiation (absorption, emission, scattering) signatures for comparison.

11 Claims, 3 Drawing Sheets

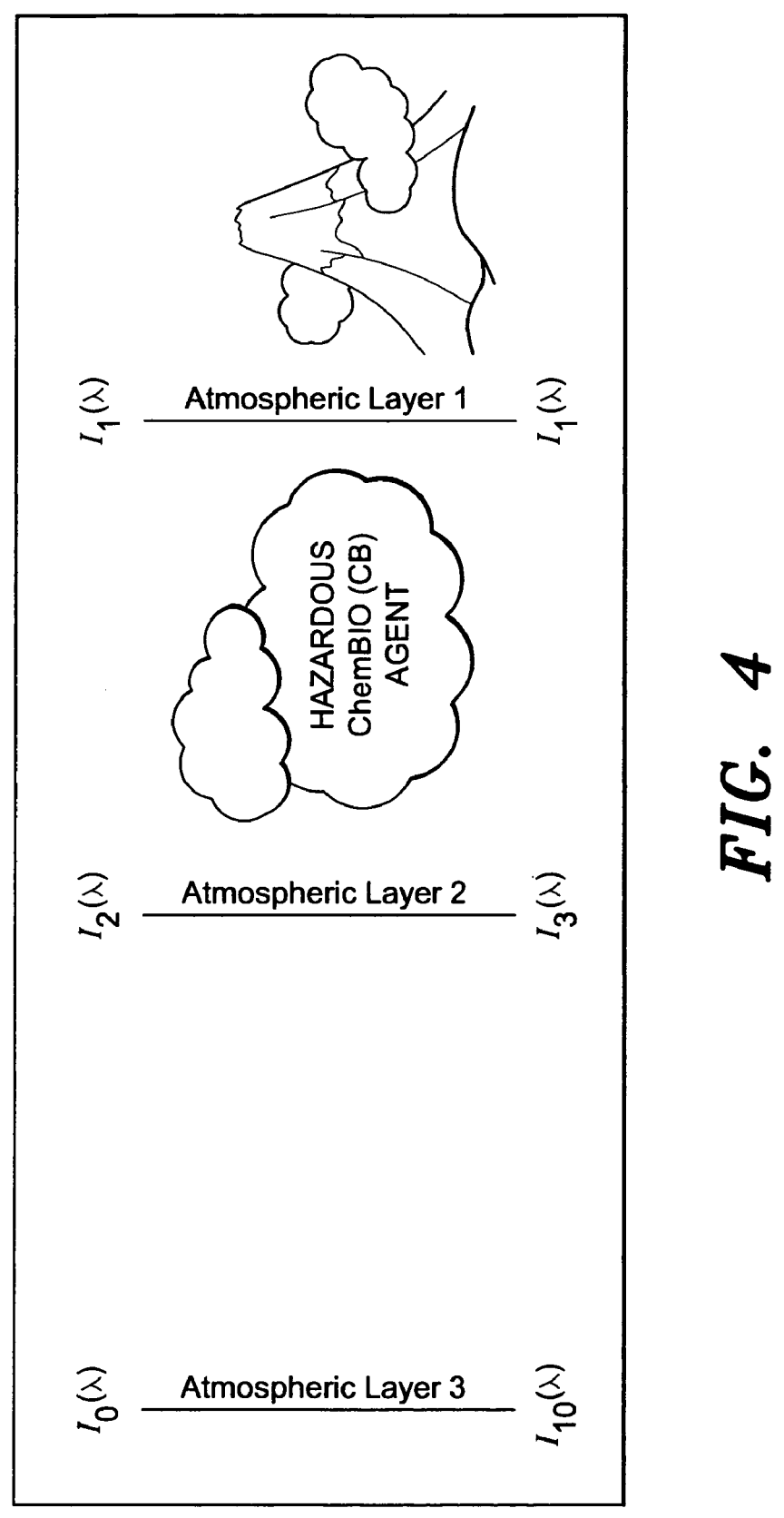

$I_1(\lambda)$ Atmospheric Layer 1 $I_1(\lambda)$

HAZARDOUS
ChemBIO (CB)
AGENT $I_2(\lambda)$ Atmospheric Layer 2 $I_3(\lambda)$ $I_0(\lambda)$ Atmospheric Layer 3 $I_{10}(\lambda)$

*FIG. 4*

TACTICAL CHEMICAL BIOLOGICAL THREAT DETECTION

FEDERALLY SPONSORED RESEARCH AND FEDERAL LICENSE RIGHTS IN THE INVENTION

Not applicable as to federally sponsored research; however the application was made under employment by a federal agency which has granted the inventor rights in the invention and in return the inventor expressly grants a non-exclusive, irrevocable, royalty-free license to the Government of the United States with power to grant licenses for all governmental purposes.

CLAIM FOR PRIORITY AND CROSS-REFERENCE TO RELATED APPLICATIONS

This application claims the priority of prior pending patent application Ser. No. 12/926,061 filed on Oct. 25, 2010 by Ravinder P. Lall, and also the priority of Provisional Patent Application Ser. No. 61/254,780, filed on Oct. 26, 2009.

SEQUENCE LISTING OR PROGRAM

Not Applicable

FIELD OF THE INVENTION

The present invention relates to a chemical and biological threat detection system using an optical sensor operating at infrared wavelengths. The system of the present invention is particularly useful in detection of biological and chemical threats at a distance.

BACKGROUND OF THE INVENTION

In the field of biological and chemical threat detection, many technologies have been developed. Many rely upon obtaining a sample of the material to be tested, and then performing various tests such as measuring the absorption spectrum, radiation spectrum, and analyzing the chemical composition using traditional tests used in chemistry and biology.

However, the prior art does not provide a way of detecting possible airborne chemical or biological threats at a distance. Optical tests have been limited by the absorption of light in the atmosphere.

SUMMARY OF THE INVENTION

From the foregoing, it is seen that it is a problem in the art to provide a system meeting the above requirements. According to the present invention, a system and process are provided which meets the aforementioned requirements and needs in the prior art. Specifically, the system according to the present invention provides a system and method for detection of chemical and biological threats using an optical sensor operating at infrared wavelengths.

More particularly, the invention relates to a system and method for detection of chemical and biological threats using an optical sensor operating at infrared wavelengths, wherein a ratio of two intensities are measured at two different, specific infrared wavelengths.

Other objects and advantages of the present invention will be more readily apparent from the following detailed description when read in conjunction with the accompanying drawings.

BRIEF DESCRIPTION OF THE DRAWINGS

FIG. 4 is a schematic view of a large area which includes three atmospheric layers and a cloud having chemical biological agents, which depicts parameters for analysis.

DETAILED DESCRIPTION OF THE INVENTION

Figure 1:
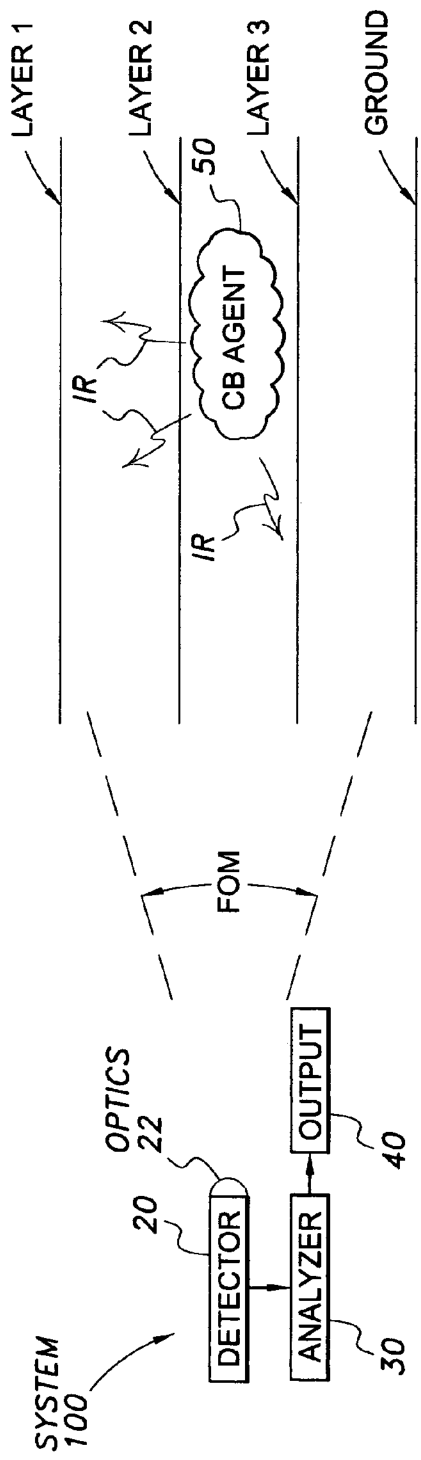
FIG. 1 is a schematic view of a system having a detector and analyzer according to the invention, receiving infrared radiation from a large area which includes three atmospheric layers and a cloud having chemical biological agents.

FIG. 1 is a schematic view of a chemical biological threat detection system 100 having a detector 20 with optics 22 which receives infrared radiation IR from a field of monitor FOM. The detector 20 sends an output signal 21 to an analyzer 30 which analyzes the received signal 21 and produces an output signal which is supplied as an output 40.

In FIG. 1, three atmospheric layers are shown, layer 1, layer 2, and layer 3. For illustration purposes, a cloud 50 is depicted which contains a chemical biological agent, the cloud 50 being located between atmospheric layer 2 and atmospheric layer 3. The detector 20 receives the infrared radiation IR from a large area which includes three atmospheric layers and a cloud having chemical biological agents. The optics 22 can be of any conventional components capable of receiving infrared radiation at a wavelength of 8-12 μM.

The operation and use of the elements of the system 100 of FIG. 1 are described further hereunder. It will the understood that the detector 20 and its field of monitor FOM can be directed at the cloud 50 from any vantage point, including from the ground, from an aircraft, and from a satellite, for example.

Figure 2:
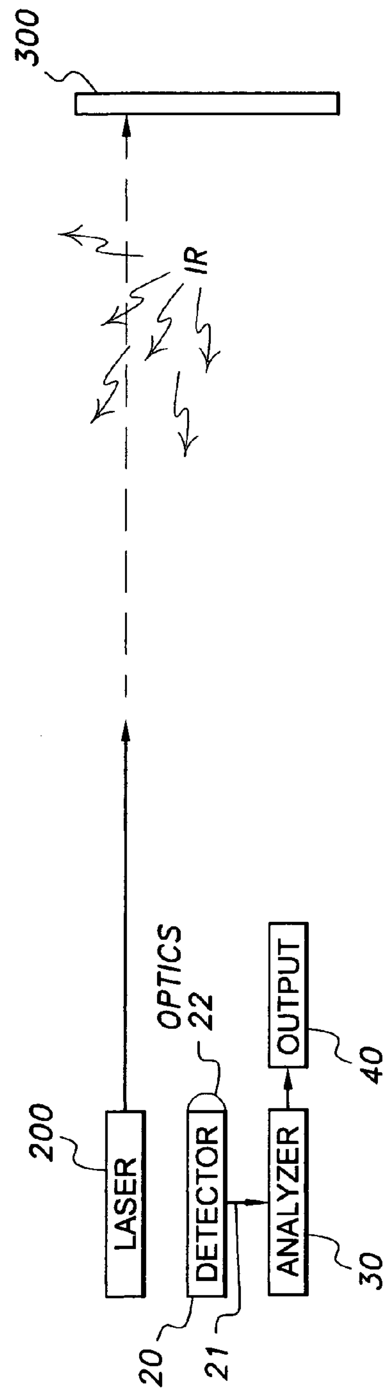
FIG. 2 is a schematic view of a system having a detector and analyzer according to the invention, receiving infrared radiation from an area produced by a target which is illuminated by a laser.

FIG. 2 is a schematic view of the detector 20 and the analyzer 30 of FIG. 1, receiving infrared radiation IR from an area illuminated by infrared radiation produced by a target 300 which is illuminated by a laser 200. The laser 200 provides the energy for producing the infrared radiation from the target 300.

Figure 3:
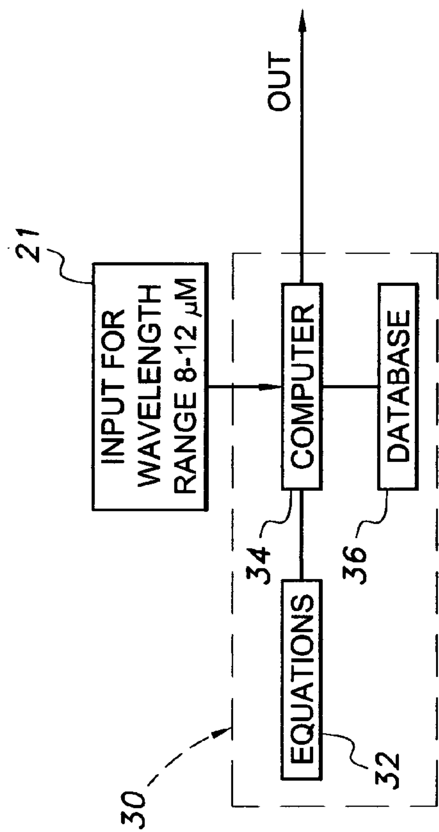
FIG. 3 is a schematic view of the components of the analyzer of FIG. 1, having a computer, a database, and which uses a set of reference equations.

FIG. 3 is a schematic view of the components of the analyzer 30 of FIG. 1. Here, the analyzer 30 is shown as having a computer 34, a set of reference equations 32, and a database 36. The analyzer 30 receives the input signal 21 as shown in FIGS. 1 and 2. The reference equations are used to analyze the data, and include those discussed further hereunder.

The following is an introduction and discussion of the invention. This relates to a chemical biological (CB) defense technology solution for enhancing the discrimination in chemical biological threat detection in atmospheric air, low level chemical biological threat detection in air, as well as tactical determination of threat chemical biological agents' concentrations in a specific atmospheric range, at various time intervals. This uses the concept of quantitative monitoring of the atmospheric air for chemical biological threats, as well as measuring the quantitative correlations/ratios in differential changes in the air, for the active/passive chemical biological Infrared (IR) EM radiation at an 8-12 μM wavelength, absorption/emission/scattering, using Electro-Optics. This chemical biological solution will use the reference chemical biological IR EM radiation (absorption, emission, scattering) signatures for comparison.

This effort is a focus of national defense for combating the weapons of mass destruction. chemical biological (CB) defense programs. The chemical or biological (COB) threats are of many types, and this term will be understood with reference to the prior art. Defense technology solutions for tactical improvements of chemical biological threat detection of this invention detect electro-magnetic radiation (photons) of 8-12 μM wavelength. The electro-optics include enhancements in discrimination for detecting minimum detectable chemical biological agent concentrations in COB threat detection, by the use of quantitative correlations/ratios of chemical biological electro-magnetic (EM) radiation (photons), in the range of 8-12 μM wavelengths. This includes use of electro-optics.

For example, bacillus subtilis bacteria and Kaolin interference have been chosen for comparison, for demonstrating this defense technology solution. Dealing with the chemical biological threat detection issues, some basic relationships and concepts concerning electro-magnetic (EM) theory and radioactive processes are also important. The part of the electromagnetic spectrum that is important in remote sensing covers wavelengths of the order 0.1 μm (UV) to 100 m (Radio HF). For wavelengths of 8-12 μm, the atmosphere is more transparent with structures from absorbing species. For dealing with standoff chemical biological detection issues, some basic relationships and concepts concerning electro-magnetic (EM) and radioactive processes are also important.

As noted above, for wavelengths of 8-12 μm, the atmosphere is more transparent with structures from absorbing species. Information on remote sensing of the atmosphere may be obtained from the following resources: REES 2001; Bruiser et al 1999; Brasseur and Solomon, 1986; Harvey; 2000; Finlayson-Pitts, 20003-9. Following quantitative correlations/ratios of electromagnetic radiation emission (photons) 8-12 μm have been described earlier, by Ravinder Lall. Significant information includes: (1) Percentage of total infrared emission energy in various spectral intervals; and (2) Relative Differential radiance Distribution. These may be used in conjunction with chemical biological agents' molecular recognition signatures (which in the present invention are stored in the database 36), in the EM spectrum being used for chemical biological detection presently.

Previous efforts in the direction of making tactical improvements in the chemical biological defense programs in chemical biological threat detection, in the area of discrimination in chemical biological threat detection, in combined efforts in the ease in chemical biological detection, as well as tactical chemical biological threat detection, are for range concentrations without the use of a multiple IR sensor network. It is important that the distinction is clear between the issue of chemical biological threat detection and the instrument detectability of the chemical biological threat. Although the two are related to some extent, they are different in many respects. The instrument detectability issue relates more to the methodologies adopted by the instruments in use, while the overall threat chemical biological detection is not just a factor of the instrument factors, but is part of an overall chemical biological threat detection strategy.

Methodology:

The methods and analysis techniques used in this invention are discussed below.

The basic equation of absorption spectroscopy, describing pure absorption of a single species in a homogeneous media is Beer-Lamberts law:

$$I(\lambda\Gamma)=I_0(\lambda)e^{L\sigma(\lambda)n}$$

where I is the measured intensity, the unattended reference intensities, L the pathlength in meters, σ(λ) the wavelength dependent absorption cross-sections ($m^2$ molecule $^{-}1$) and n the number density of the species [molecules $m^{-3}$). The dimensionless quantity Lσ(λ)n is often referred to as the optical depth, denoted τ.

The four basic laws of IR radiation used are Kirchhoff's law, Planck's law, the Stefan-Boltzmann law, and Lambert's cosine law. These four laws will be used as needed. The spectral radiance, emitted radiation from a black body is a function of temperature and will be distributed according to the Planck distribution. It is noted that the black body radiation law doesn't hold for free molecules where absorption and emission of a photon takes place in a very small wavelength region corresponding to the energy of transitions. Electromagnetic radiation is generated by transformation of energy from other forms such as kinetic, chemical, thermal, electric, magnetic, or nuclear. Heat energy is the kinetic energy of random motions of the particles of matter. The emission energy in the approach described above may be due to kinetic energy.

Under atmospheric conditions Rayleigh and Mie scattering also contribute to the radiation extinction by scattering light away from the line of sight. In the present studies known in this technical field, it is assumed that the Rayleigh and Mie scattering contributions are negligible. All atmospheric species that have significant absorption cross-sections must be included. The theoretical detection limit Nlim for a particular species and wavelength can be estimated, if σ', L, and the minimum detectable differential optical depth $\Gamma'_{lim}$ are known. In order to correctly apply the Electro-optics technology techniques for the detection of various number densities of chemical biological Threat agents, corrections must be applied to the measured spectra, and absorption resections. Errors due to instrument resolution and sampling, polarization response, wavelength shifts, temperature dependence, or ring contributions, might for example may be considered (Platt et al, 1997). Generally the concentrations of the studied species are inhomogenous along the line of sight.

Chemical Biological Threat Detection System

The following is a brief description of the development of the chemical biological threat detection system, for quantitative monitoring of the differential changes in EM energy caused by the entry of the hazardous chemical biological agents into the field of monitor (FOM). These may be representative of certain specific chemical biological agents. These quantitative chemical biological IR EM correlations/ratios, at various wavelengths (λ), are found by correlating with the quantitative low level detection of the change in measured EM energy (8-12 μM wavelength), for different atmospheric layers (layers 1, 2, and 3 of FIG. 1 for example), for a specific monitored field of view (FOM)/line of sight.

The term $I_1(\lambda)$ is the EM radiation (photons), intensity, for wavelength for a wavelength, λ, (8-12 μM wavelength), at the atmospheric layer immediately above the target chemical biological agent cloud. The term $I_2(\lambda)$ is the EM radiation (photons) intensity, for a wavelength λ, (8-12 μM wavelength), at the atmospheric layer immediately below the target chemical biological agent cloud. The term $I_0(\lambda)$ is the measured EM radiation (photons) intensity (λ) for that particular FOV/line of sight. The term $W(M^{-2}, Sr^{-1}, M^{-1})$, where Sr is measured in steradians, is the solid angle for that FOM, for the target chemical biological agent cloud. The term $n_{21air}$ is the molecule/particle number density of all the atmospheric air particles/atmospheric air components $n_{21}$=na+$n_b$+$n_c$ . . . ), encountered by the EM radiation energy during traveling through the volume $V_1$, for the FOM.

The parameters listed above are at similar atmospheric parameters of temperature, and pressure, humidity etc., where the term $n_{cb}$ is the number molecule/particle density of the target chemical biological threat agent, as well as other atmospheric air components encountered, after the entry/influx of the target chemical biological threat agent, in the same volume $V_1$ of the FOM at the specific coordinates of the line of sight. It is assumed that, immediately after the influx of the chemical biological agent, most of the particle number density between atmospheric layers 1 and 2 consists of chemical agent molecular density or biological agent particle density, as applicable.

Let the term σcb(λ) be the absorption cross section for that specific chemical biological agent that made its entry/influx into the FOM. In this case the total IR EM measurements for the FOM under consideration are made after the transient period, then the diffusion of the chemical biological agent into the overall FOM will have to be taken into consideration. Let the term $I_0$ be the EM radiation for the specific FOM, as measured at the specific coordinates for the point of chemical biological threat monitor, fixed or movable. Let the term $I_{10}$, represent the measured IR EM intensity.

FIG. 4 is a schematic view of a large area which includes three atmospheric layers and a cloud having chemical biological agents, which depicts parameters for analysis. In FIG. 4, a model is shown for measured and theoretical differential changes in IR EM energy (photons) (8-12 μM) after entry of hazardous chemical/biological (CB) agents into the specific field of view of the chemical biological threat monitor (CBT-FOM)).

In this figure, the change in EM energy (photons) for wavelength by traveling through the atmospheric layer 1 to the atmospheric layer 2, is shown from above as shown before the influx of the target chemical biological agent in the field of monitor (FOM). For all notations, and assumptions used, please refer to the foregoing discussion hereinabove.

$$\ln\left(\frac{I_1}{I_2}\right)\lambda = V_1\sigma_{air(\lambda)}n_{21air(\lambda)}$$

The change in EM energy (photons) for wavelength (λ) (8-12 μM), by traveling through the atmospheric layer 1 to the atmospheric layer 2, as shown above, after the influx of the chemical biological agent in the FOM, is given by:

$$\ln\left(\frac{I_1}{I_3}\right)\lambda = V_1\sigma_{CB(\lambda)}n_{3CB}$$

This change in EM energy is a function of the nature of the material for the unknown chemical biological agent, entered in the (CBTFOM.)

The change in EM energy (photons) for wavelength (λ) (8-12 μM), before the entry of the specific unknown chemical biological agent by traveling through the atmosphere Layer 1 to the atmosphere Layer 3, to the specific coordinates for the place of monitoring & EM energy measurements, is given by:

$$\ln\left(\frac{I_1}{I_0}\right)\lambda = \sigma_{air(\lambda)}n_{01air}$$

The change in EM energy (photons) for wavelength (λ) (8-12 μM) by travelling through the atmosphere Layer 1 to the atmosphere layer 3, to the specific coordinates, for the place of monitoring & EM energy measurements, is given by $$\ln\left(\frac{I_1}{I_10}\right)\lambda = V_1\sigma_{CB(\lambda)}n_{3CB} + V_{01}\sigma_{air(\lambda)}n_{01air} - V_1\sigma_{air(\lambda)}n_{21air}.$$

This can be simplified in the following steps.

$$\ln\frac{(I_0)\lambda}{(I_{10})\lambda} = \ln\left(\frac{I_2}{I_3}\right)\lambda$$

$$\frac{\ln\left(\frac{I_0}{I_{10}}\right)\lambda_1}{\ln\left(\frac{I_0}{I_{10}}\right)\lambda_2} = \frac{\ln\left(\frac{I_2}{I_3}\right)\lambda_1}{\ln\left(\frac{I_2}{I_3}\right)\lambda_2}.$$

This can be shown to be equal to;

$$\frac{-\sigma_{air(\lambda_1)}n_{21air} + \sigma_{CB(\lambda_1)}n_{31CB}}{-\sigma_{air(\lambda_2)}n_{21air} + \sigma_{CB(\lambda_2)}n_{31CB}} \quad \text{(A)}$$

Applying the ratios of the product for multiple correlations for CBIREM radiation between 8-12 μM. In accordance with the assumptions stated above, if the chemical biological threat agent enters/influxes into the FOM during CBT monitoring and measuring, the EM energy intensity $I_0$, (λ) and $I_{10}$, (λ), the EM energy change contribution due to number molecule density for atmospheric air components may be neglected, as a result the following expression becomes zero.

$$\sigma_{air(\lambda)}n_{21air} = 0$$

Hence $$\frac{\ln\left(\frac{I_0}{I_10}\right)\lambda_1}{\ln\left(\frac{I_0}{I_10}\right)\lambda_2} = \frac{\sigma_{CB(\lambda_1)}n_{31CB}}{\sigma_{CB(\lambda_2)}n_{31CB}}$$

As is seen, from the above expression, this expression, for quantitative correlations ratios, of the unknown chemical biological threat agent that enters the CBTFOM, can be found by the direct monitoring of $I_0$(λ) and $I_{10}$(λ) after some time from the time of entry of the chemical biological agent.

Results and Discussion:

For a continuous surveillance/chemical biological threat monitoring with specific coordinates for FOM with a chemical biological threat detection system, this just reduces to continuous determination of I((λ) for a specific CBTFOM, for different wavelengths, for a specific wavelength range, which is 8-12 μM.

As is seen, this will be a quantitative chemical biological threat detection approach that will allow the chemical biological EM correlations/ratios determination as a function of the measured monitored EM energy changes, for a specific field of CBT monitor. These chemical biological EM energy correlations/ratios for different sets of wavelengths/wavelength intervals as a function of chemical biological absorption cross section ratios, at the same wavelengths, can be compared with the known chemical biological energy changes, correlation/ratios, and at similar atmospheric conditions of temperature, pressure, etc.

As this expression above is just a function of two wavelengths, it may be used for any wavelength range, along as allowed by the EM energy measurement capability of a specific chemical biological detection system, as well as the choice of the source of the EM energy, being exploited for the chemical biological threat detection, such as the EM energy from the Sun, the EM energy from the earth, or from lasers being used as a source of energy for a specific wavelength interval. This can be based upon the knowledge of IR absorption spectra for various chemical biological threat agents for investigation. This may be a very quantitative method for chemical biological threat detection as this does not limit to the FOM/line of sight used for EM energy changes measurements. The total path length encountered by the incoming electromagnetic radiation consists of the path length of the sudden influx of the chemical biological agent cloud as well as the path length imposed by the atmospheric chemical biological species in the way from the agent cloud to the sensor. Depending upon the timings of measurements from the time the chemical biological agent cloud enters the FOV, the atmospheric parameters of the wind speed, etc., the transient imaginary atmospheric demarcation line separating the atmospheric layer in the field of view (CB IR EM Radiation sensor), changes. This information about the chemical biological cloud combined with the atmospheric components, is compared with the region of the FOV that contains just the rest of the atmospheric components. After some time the chemical biological agent cloud reaches equilibrium with the rest of the atmospheric components in the FOV.

For chemical biological threat detection purposes, initially it will be of interest to know the immediate presence of the chemical biological agent in the line of sight, as well as it will be of interest to monitor later the level of the chemical biological agent in the line of sight. The amount of light being absorbed by the particular species depends upon the total impact on the atmospheric composition by the influx of that species. After some time equilibrium is reached and the total photons absorption due that species depend upon the total number of photons being absorbed by the particular species can be found by finding the ratio of different amounts of light absorbed in the total field of view by that particular species. If the initial hazard is detected at that level of the hazard distribution in the atmosphere, and the impact on the people in the surrounding areas may be assessed, it may be correlated with a Hazard Prediction and Assessment Capability model, which predicts the hazard prediction.

CONCLUSIONS

As shown above, a chemical biological threat detection system is developed. This system is based on the quantitative correlations/ratios of chemical biological IR EM energy (photons), found in terms of differential, as well as total absorption/emission, for a specific wavelength range for the unknown chemical biological threat agent. This is ideally suited for continuous chemical biological threat monitoring. The potential of this chemical biological threat detection model lies in the fact that the only measurable parameter in this is the intensity of the EM energy, for a specific wavelength range, and it can exploit the maximum amount of the chemical biological agent material suspected release for detection, depending upon the capability of the chemical biological detection system used, for measurement of the EM energy changes, for a specific wavelength range. It can be used with broad sources of EM energy, such as Sun/earth, or artificial sources of light energy such as lasers (used with appropriate modifications).

The invention being thus described, it will be evident that the same may be varied in many ways. Such variations are not to be regarded as a departure from the spirit and scope of the invention and all such modifications are intended to be included within the scope of the claims.

What is claimed is:

1. A chemical biological threat detection system for detecting chemical and biological threats in atmosphere, comprising:

a laser for irradiating a field to be monitored, for exciting components in the field of monitor such that at least a portion of the components in the field of monitor are caused to emit IR radiation in a wavelength range 8-12 μM wavelength;

a detector having a field of monitor, for continuously detecting incoming infrared radiation in the wavelength range 8-12 μM wavelength; said detector continuously monitoring the field of monitor on a continuing basis such that it can detect a change in the field of monitor upon entry of an unknown biological threat agent;

an analyzer having reference equations, a reference database, and a computer, for determining quantitative correlations ratios of the unknown chemical biological threat agent that enters the field of monitor of the detector, using direct measurements of $I_0(\lambda)$ and $I_{10}(\lambda)$; and the quantitative chemical biological IR EM correlations ratios, at various wavelengths (λ), being found by correlating with the quantitative low level detection of the change in measured EM energy (8-12 μM wavelength), for at least two different atmospheric layers, for a specific monitored field of view.

2. A chemical biological threat detection system as claimed in claim 1, where the quantitative chemical biological IR EM correlations ratios are found for three different atmospheric layers, for said specific monitored field of view.

3. A chemical biological threat detection system as claimed in claim 1, where the calculations are performed in accordance with Beer-Lamberts law for a single species in a homogeneous media, namely:

$$I(\lambda'\Gamma)=I_0(\lambda)e^{-L\sigma(\lambda)n}$$

where I is the measured intensity, L the pathlength in meters, $\sigma(\lambda)$ the wavelength dependent absorption cross-sections ($m^2$ molecule $^{-}1$) and n the number density of the species in units of molecules $m^{-3}$, and wherein the dimensionless quantity $L\sigma(\lambda)n$ is the optical depth, denoted $\tau$.

4. A chemical biological threat detection system as claimed in claim 1, wherein the calculations are performed based on Kirchhoff's law, Planck's law, the Stefan-Boltzmann law, and Lambert's cosine law.

5. A method for detecting chemical and biological threats in atmosphere, comprising:

irradiating a field to be monitored, for exciting components in the field of monitor such that at least a portion of the components in the field of monitor are caused to emit IR radiation in a wavelength range 8-12 μM wavelength;

providing a chemical and biological threat detection system having a detector which has a field of monitor, for continuously detecting incoming infrared radiation in the wavelength range 8-12 μM wavelength and having an analyzer having reference equations, a reference database, and a computer, for determining quantitative correlations ratios of the unknown chemical biological threat agent that enters the field of monitor of the detector, using direct $I_0(\lambda)$ and $I_{10}(\lambda)$; and using the computer to determine a ratio of $I_0(\lambda)$ and $I_{10}(\lambda)$ for comparison with the reference database to detect chemical and biological threats;

the quantitative chemical biological IR EM correlations ratios, at various wavelengths (λ), being found by correlating with the quantitative low level detection of the change in measured EM energy (8-12 μM wavelength), for at least two different atmospheric layers, for a specific monitored field of view.

6. A chemical biological threat detection system as claimed in claim 5, wherein in the step of using the computer, the quantitative chemical biological IR EM correlations ratios are found for three different atmospheric layers, for the monitored field of view.

7. A chemical biological threat detection system as claimed in claim 5, wherein in the step of using the computer, the calculations are performed in accordance with Beer-Lamberts law for a single species in a homogeneous media, namely:

$$I(\lambda T)=I_0(\lambda)e^{-L\sigma(\lambda)n}$$

where I is the measured intensity, L the pathlength in meters, σ(λ) the wavelength dependent absorption cross-sections ($m^2$ molecule $^{-1}$) and n the number density of the species in units of molecules $m^{-3}$, and wherein the dimensionless quantity $L\sigma(\lambda)n$ is the optical depth, denoted τ.

8. A chemical biological threat detection system as claimed in claim 5, wherein in the step of using the computer, the calculations are performed based on Kirchhoff's law, Planck's law, the Stefan-Boltzmann law, and Lambert's cosine law.

9. A method for detecting chemical and biological threats in atmosphere, comprising:

in an active mode, irradiating a field to be monitored, for exciting components in the field of monitor such that at least a portion of the components in the field of monitor are caused to emit IR radiation in a wavelength range 8-12 μM wavelength;

providing a chemical and biological threat detection system having a detector which has a field of monitor, for detecting incoming infrared radiation in the wavelength range 8-12 μM wavelength and having an analyzer having reference equations, a reference database, and a computer, for determining quantitative correlations ratios of the unknown chemical biological threat agent that enters the field of monitor of the detector, using direct $I_0(\lambda)$ and $I_{10}(\lambda)$;

said detector being capable of operating in either of a passive mode and said active mode, wherein in said passive mode, the field of monitor is not irradiated and instead passively senses naturally-occurring incoming infrared radiation in the wavelength range 8-12 μM wavelength; and using the computer to determine a ratio of $I_0(\lambda)$ and $I_{10}(\lambda)$ for comparison with the reference database to detect chemical and biological threats in both said active mode and in said passive mode; and wherein in the step of using the computer, the quantitative chemical biological IR EM correlations ratios are found for three different atmospheric layers, for the monitored field of view.

10. A chemical biological threat detection system as claimed in claim 9, wherein in the step of using the computer, the calculations are performed in accordance with Beer-Lamberts law for a single species in a homogeneous media, namely:

$$I(\lambda T)=I_0(\lambda)e^{-L\sigma(\lambda)n}$$

where I is the measured intensity, L the pathlength in meters, σ(λ) the wavelength dependent absorption cross-sections ($m^2$ molecule $^{-1}$) and n the number density of the species in units of molecules $m^{-3}$, and wherein the dimensionless quantity $L\sigma(\lambda)n$ is the optical depth, denoted τ.

11. A chemical biological threat detection system as claimed in claim 9, wherein in the step of using the computer, the calculations are performed based on Kirchhoff's law, Planck's law, the Stefan-Boltzmann law, and Lambert's cosine law.

* * * * *